United States Patent [19]

Rasmussen

[11] Patent Number: 5,725,534
[45] Date of Patent: Mar. 10, 1998

[54] METHOD OF MANUFACTURING AN ASSEMBLY FOR POSITIONING AN EMBOLIZATION COIL IN THE VASCULAR SYSTEM, AND SUCH AN ASSEMBLY

[75] Inventor: Erik Edelboe Rasmussen, Soeborg, Denmark

[73] Assignee: William Cook Europe A/S, Denmark

[21] Appl. No.: 484,854

[22] Filed: Jun. 7, 1995

[30] Foreign Application Priority Data

Jan. 3, 1995 [DK] Denmark .................. 0005/95

[51] Int. Cl.$^6$ ............................................. A61B 17/00
[52] U.S. Cl. ................................ 606/108; 128/772
[58] Field of Search .................... 606/108; 128/772

[56] References Cited

U.S. PATENT DOCUMENTS

| | | |
|---|---|---|
| 4,994,069 | 2/1991 | Ritchart et al. . |
| 5,122,136 | 6/1992 | Guglielmi et al. . |
| 5,234,437 | 8/1993 | Sepetka ........................... 606/108 |
| 5,250,071 | 10/1993 | Palermo . |
| 5,267,573 | 12/1993 | Evans et al. .................... 128/772 |
| 5,273,042 | 12/1993 | Lynch et al. .................... 128/772 |
| 5,282,479 | 2/1994 | Havran ........................... 128/772 |
| 5,297,546 | 3/1994 | Spofford et al. ............. 128/207.014 |
| 5,366,444 | 11/1994 | Martin ........................... 128/772 |

FOREIGN PATENT DOCUMENTS

| | | |
|---|---|---|
| 2684305 | 6/1993 | France . |
| 9003760 | 4/1990 | WIPO . |
| 9112836 | 9/1991 | WIPO . |
| 9205829 | 4/1992 | WIPO . |
| WO9311823 | 6/1993 | WIPO . |
| WO9311825 | 6/1993 | WIPO . |

OTHER PUBLICATIONS

Lund, Gunnar, M.D. et al. "Detachable Steel Spring Coils for Vessel Occlusion"; *Radiology*; May 1985, p. 530.

*Primary Examiner*—Robert A. Hafer
*Assistant Examiner*—Benjamin K. Koo
*Attorney, Agent, or Firm*—Richard J. Godlewski

[57] ABSTRACT

An assembly for positioning an embolization coil (4) in the vascular system. The assembly includes a guidewire having a relatively flexible distal section (6), which has a central core (7) and a threading coil (10), the distal turns (11) of which are arranged with such mutual spacing (12) that the embolization coil can be threaded in and out of the threading coil. The distal end section of the guidewire is manufactured with an elongated, rotationally symmetrical member, such as cylindrical member (13), and the peripheral surface of the member is provided with a bonding layer (25). Then the distal turns of the threading coil are positioned in the desired helical shape on the external side of the member, and the bonding layer is activated so that the distal turns are fixed to the member in this shape. The cylindrical member (13) has an outer diameter which is a fraction smaller than the inner diameter of the embolization coil (4) and has a length which is longer than the extent in the axial direction of the guidewire of at least three of the distal turns (11) of the threading coil. The distal turns of the threading coil are fixed to the external side of the member, so that the thread provided is geometrically stable and smooth-running.

8 Claims, 6 Drawing Sheets

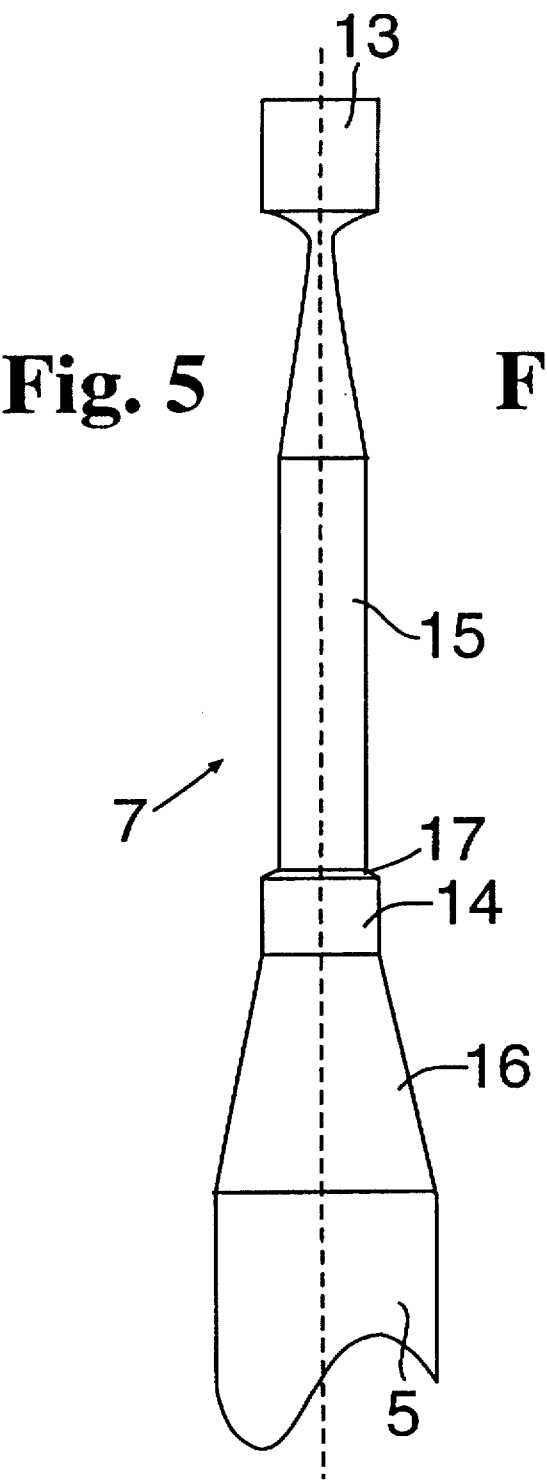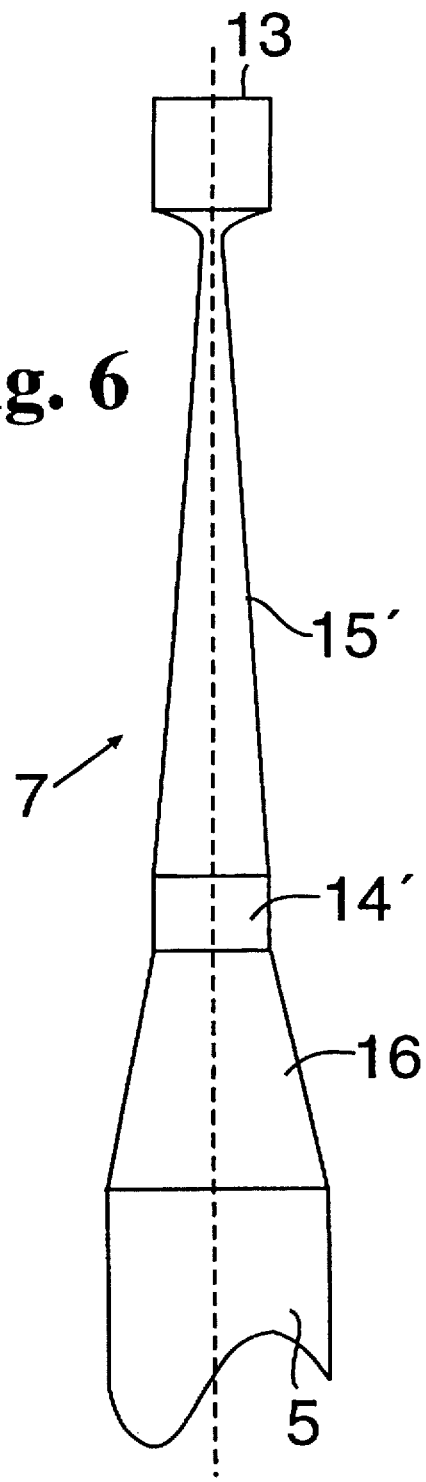

METHOD OF MANUFACTURING AN ASSEMBLY FOR POSITIONING AN EMBOLIZATION COIL IN THE VASCULAR SYSTEM, AND SUCH AN ASSEMBLY

TECHNICAL FIELD

The present invention relates to a method of manufacturing an assembly for positioning an embolization coil in the vascular system, which assembly comprises a guidewire having a relatively flexible distal section which has a central core and a threading coil, the distal turns of which are arranged with such mutual spacing that the embolization coil can be threaded in and out of the threading coil, and the invention further relates to such an assembly.

BACKGROUND OF THE INVENTION

The journal *Radiology*, May 1985, page 530, "Detachable Steel Spring Coils for Vessel Occlusion" by Gunnar Lund et al., describes such an assembly where the distal turns of the wirecoil of the guidewire are pulled out into a helical shape by means of pliers to create spaces between the turns, into which the embolization coil can be threaded. A safety thread constituting the distal end of the central core is axially movable in relation to the distal turns of the guidewire. The safety thread prevents the embolization coil from falling sideways out through the turns of the guidewire during insertion through the catheter, but some sideways displacement may occur, as the outer diameter of the safety thread is substantially smaller than the inner diameter of the embolization coil. This problem can be reduced by using a core of a larger diameter, but such a core will have a rigidity which renders difficult or prevents advancement of the embolization coil to aneurysms in narrow blood vessels difficult of access, where the path of advancement typically exhibits sharp changes of direction, i.e., aneurysms which can only be reached through superselective catheterization.

When an embolization coil is to be positioned in an aneurysm or at any other place in the vascular system, where it is desired to create a physical barrier against blood flow, for example, for interruption of the blood supply to tumors, to arterio-venous deformities or to damaged vessel areas in the brain, the backbone, the internal organs or other places with narrow vessels, access is first created to the place in question by insertion of a catheter by means of prior-art techniques.

For example, using the Seldinger technique, the catheter can be inserted transfemorally into the vascular system and be passed to the brain by means of a rotatable guidewire. When the catheter is positioned with its distal end at the desired position, the guidewire is removed, and a guidewire mounted with an embolization coil is pushed in through the catheter, until the coil has been passed distally out of the catheter. As the embolization coil is threaded into the guidewire, it is possible for the radiologist to check whether the size and shape of the coil are suitable for the site in question before the coil is released, and to retract the coil into the catheter and out of the patient, if the coil turns out to be unsuitable.

When a suitable embolization coil has been positioned at the desired site, the coil is released by rotating the guidewire, until the coil is threaded out of the guidewire. When the guidewire is rotated to thread out the coil, a torsional deformation of the distal turns may occur in the above prior-art assembly, which causes a risk of locking the embolization coil to the guidewire so that threading out is rendered difficult or prevented. Additionally, considerable friction may occur between the guidewire and the internal side of the catheter so that the wirecoil at the distal end of the guidewire is locked to the catheter and prevents further rotation.

PCT published specification No. WO93/11823 describes an assembly in which the core at the distal end of the guidewire is provided with two axially spaced soldered-on semispherically shaped radial enlargements, to which the distal and the proximal ends, respectively, of a threading coil are fastened so that an embolization coil may be threaded in or out of the threading coil. The distal enlargement can typically have a diameter between 0.16 and 0.60 mm, and the proximal enlargement a diameter between 0.2 and 0.9 mm. The diameter of the core at the soldering sites is substantially smaller than the enlargements, which renders it extremely difficult in terms of production technique to manufacture the assembly with the solders without any risk of functional failure. This known assembly also suffers from the above disadvantage that the threading coil can be distorted at the threading out with a consequent risk of locking the embolization coil to the guidewire. As the two coil wires threaded together are in close contact with each other, there is noticeable friction between the wires. A sleeve may be inserted between the guidewire and the catheter and be made to engage with and hold the proximal end of the embolization coil during threading out, but as the wall thickness of this sleeve is less than 0.1 mm, it only has little compressive strength, which renders it difficult to hold the coil during threading out.

A number of other methods of controlled release of embolization coils are known. In patent publications WO93/11825 and U.S. Pat. No. 5,250,071, a releasable geometrical locking is used between the coil and the distal end of the guidewire, and in patent publication U.S. Pat. No. 5,122,136 the coil is connected with the guidewire through thin connecting areas which are electrolytically eroded away when the coil is positioned at the desired site, while U.S. Pat. No. 4,994,069 provides an adhesive fastening of the coil to the guidewire, and a release by heating of the adhesive layer with laser energy supplied through an optical fibre. These known assemblies are either difficult to manufacture and/or time-consuming or difficult to detach.

SUMMARY OF THE INVENTION

The object of the invention is to provide a method and an assembly which on one hand provide a simple and reliable manufacture of the assembly in the small dimensions of material required for advancing embolization coils into very small vessels, and on the other hand make available to the radiologist an assembly which is simple and quick to operate in a safe manner and permits fully controllable pushing out of the coil from the catheter and repositioning of the coil in the catheter, until the radiologist accepts the position and size of the coil, whereupon the coil can be threaded out and released in a simple and rapid manner with great safety.

In view of this object, the method according to the invention is characterized in that the distal end of the guidewire is formed with an elongated, rotationally symmetrical member, such as a cylindrical member, that a bonding layer is applied to the peripheral surface of the member and the distal turns of the threading coil are arranged in the desired helical shape on the external side of the member, and that the bonding layer is activated so that the distal turns are fixed to the member in this shape.

As a bonding layer is applied to the whole periphery of the rotationally symmetrical member, the application may be carried out in a simple manner by spreading or spraying on of or brief immersion into the desired bonding layer material. The bonding layer may be applied before, in connection with, or after the distal turns are pulled over the member, whereupon the bonding layer is activated for fixation of the turns. If the bonding layer is exclusively applied before the turns are arranged in the desired shape, activation of the bonding layer may consist of an action which creates a bond between the turns and the bonding layer. If, alternatively, the bonding layer is applied in ample quantities after the turns have been arranged on the elongated member, for example, by immersing the member with the turns into bonding layer material, the activation of the bonding layer may involve a removal of excess bonding layer material.

Threading the embolization coil in and out is facilitated by the fact that the geometry of the turns is locked after fixation on the member, which prevents deformation of the turns. By adjustment of the axially directed pull in the turns, their pitch can easily be adjusted, i.e., the spacing between the turns can easily be adjusted according to wire thickness and the pitch of the embolization coil, so that the latter can be threaded into or out of the thread formed by the turns on the external side of the member with a minimum of friction. At the activation of the bonding layer, the axial position of the turns in relation to the member may be adjusted.

Preferably, the bonding layer is a soldering or brazing material, such as tin or silver, which is activated by heat influence, as the soldering or brazing material is easy to apply in a thin layer on the rotationally symmetrical elongated member, whereupon the soldering or brazing material sets with a firm and smooth surface which is not grazed when the distal turns are pulled along the member. After the arrangement of the turns on the member, soldering or brazing material may be applied, if necessary, whereupon the bonding layer is activated by heating and any excess soldering or brazing material is drawn off.

As an alternative to soldering or brazing, the bonding layer may be an adhesive, such as a plastic, which is activated by self-curing or by irradiation with ultraviolet light. This is particularly advantageous if the material or dimensions of the turns render it undesirable to expose them to the heat influence which occurs at soldering. At the irradiation, the adhesive cures so that the turns are fixed to the member. The bonding layer may be of a self-curing adhesive material, such as epoxy resin, which, however, requires the turns to be held in or of themselves retaining the desired shape for the period of time which passes before the curing is completed.

The assembly according to the invention is characterized in that the distal section of the guidewire has an elongated, rotationally symmetrical member, such as a cylindrical member having an outer diameter which is a fraction smaller than the inner diameter of the embolization coil, and having a length which is longer than the extent in the axial direction of the guidewire of at least three of the distal turns of the threading coil, and that the distal turns of the threading coil are fixed to the external side of the member.

As indicated above, the elongated member and the distal turns fixed thereon produce a well-defined and geometrically stable thread for the proximal turns of the embolization coil, so that particularly the threading out of the coil may take place without any risk of locking inside the thread owing to guidewire torsion. The thread may be formed to be very smooth-running by fixing the distal turns of the guidewire in a helical shape having a pitch corresponding to the pitch of the proximal turns of the embolization coil in an unloaded state. If less than three of the distal turns are fixed to the external side of the member, it will be necessary to thread the coil in past the proximal end of the member, which entails a risk of locking the coil in the turns positioned at the proximal side of the member.

In a preferred embodiment, at least five, preferably from 8 to 20, of the distal turns of the threading coil are fixed to the external side of the member. The larger number of fixed turns renders it possible to thread the embolization coil further into the guidewire, which may be an advantage if the catheter has been inserted along a path with many bends, which may necessitate turns of the guidewire about its longitudinal axis to pass the bends. Even following several rotations of the guidewire in the threading-out direction, the coil will be in engagement with the thread, and following several rotations in the threading-in direction will be prevented from becoming locked at the proximal end of the thread. Thus, the long thread results in the operating advantage that the radiologist need not consider during the insertion whether the guidewire is rotated one way or the other. The long thread may give the radiologist a further advantage, if there is doubt about the most suitable coil shape or size for the embolization job in question. After pushing out the coil from the catheter, the radiologist can manipulate the coil to test whether it is suitable for the site in question, without any risk of detachment and thus loss of the coil.

In an embodiment especially suitable for superselective catheterization, the outer diameter of the member is smaller than 0.25 mm, and its length is between 2 and 4 mm. The small diameter of the member permits it to be passed out through a catheter inserted in vessels having a vessel diameter of less than from 3 to 1 mm, i.e., for example fourth or fifth order vessel branches, which may be, for example, cerebral or abdominal.

In a further embodiment which is suitable for larger vessels, the outer diameter of the member is in the interval from 0.25 to 0.36 mm, preferably at least 0.28 mm. The slightly larger dimensions of materials result in a less vulnerable assembly.

The assembly may suitably be formed so that the central core in the flexible distal section of the guidewire comprises the distal member, a proximal portion and an intermediate portion with a decreasing diameter towards the member, and that the threading coil is the distal end of a wirecoil, the proximal end of which is fastened to said proximal portion. It is well-known to use a wirecoil on the flexible distal end of a guidewire to provide the guidewire with suitable spring properties combined with the flexibility obtainable with a core having a decreasing diameter toward its distal end. Guidewires of this type have proved very suitable for superselective catheterization in numerous cases. These known advantages are retained in the embodiment, and the following further advantage has also been obtained. When the embolization coil is to be detached, the guidewire is rotated, which may result in friction locking the wirecoil against rotation to the internal side of the catheter at the places where the path of the catheter exhibits considerable changes of direction. However, the locking against rotation does not prevent continuous threading out of the embolization coil, as the core of the guidewire can freely rotate inside the wirecoil, until the embolization coil is detached. During this rotating motion, the wirecoil is twisted in the rotationally non-locked sections between the fastenings to the distal member and the proximal portion, just as when a torsional spring is tightening or relaxed on rotation.

In a particularly advantageous further development of this embodiment, the proximal portion has substantially the same diameter as the member, the intermediate portion tapers substantially evenly towards the cylindrical member where the diameter is suddenly increased to the outer diameter of the member, and the length of the member amounts to at the most a few percent of the length of the intermediate portion. The great length of the intermediate portion gives the wirecoil a correspondingly great length so that the coil can absorb the torsion of many rotations, if the coil is locked against rotation at discrete points along its length. At the same time, the even taper of the intermediate portion gives the distal section of the guidewire an evenly increasing flexibility, which is largest at the distal end immediately before the sudden increase of the diameter to the outer diameter of the member. The wirecoil may have the same inner diameter over its full length, because the proximal portion and the member have substantially the same outer diameters.

In a further embodiment, the rotationally symmetrical member has a decreasing diameter towards its distal end. A tapering may occur over the whole or part of the length of the member to produce a conical thread, which can be used for threading in of embolization coils of different diameters on one and the same guidewire, but preferably, the peripheral surface of the member with the thread has a constant diameter, and the area with decreasing diameter is positioned distally of the threaded area to facilitate the centering of the embolization coil when it is being threaded in. Such an aid for centering, known per se, is especially valuable in the assembly according to the invention, where the embolization coil may have a diameter of, for example, 0.2 mm, and where the threading in may be effected manually.

The invention further relates to an assembly for positioning of an embolization coil in the vascular system, the assembly comprising a guidewire having a relatively flexible distal section on which the embolization coil is mounted before insertion into a catheter positioned in the vascular system with its distal end arranged at the site of delivery of the embolization coil and its proximal end with associated coupling means arranged outside the vascular system, and a guidewire holder with a helically-shaped tube in which the guidewire is placed, which assembly is characterized in that the guidewire holder has a coupling means for coupling to the coupling means of the catheter, that the tube has a cut in which the guidewire is visible and can be pushed forwards manually, and that the guidewire has a marking which cooperates with the cut to indicate when the flexible section of the guidewire has been passed fully into the catheter. The guidewire holder is conventionally only used as a protective storage and transportation sleeve, which is removed before the guidewire is to be inserted into the catheter. By providing the guidewire holder with a coupling means, the holder may be connected with the inserted catheter, and the flexible distal section of the guidewire with the embolization coil can be pushed into the catheter before the holder is removed. Thus, the holder ensures centering of the guidewire opposite to the mouth of the catheter, which facilitates the operation of the assembly, and protection of the guidewire against environmental influences, which prevents a mechanical overloading of the embolization coil at the insertion. Such a security against overloading is valuable in the assembly according to the invention, because owing to its small dimensions the thread is easy to damage, and because the unproblematic threading out of the embolization coil aimed at by the invention presupposes an undisturbed thread.

The easy-to-operate design is furthermore promoted by means of the marking, which gives the radiologist an indication as to when the guidewire has been inserted so far into the catheter that the holder may be released from the catheter and be pulled off the guidewire.

In one embodiment the marking is visible in the cut, when the embolization coil is inserted through the proximal end of the catheter, where the radiologist should pass the guidewire forward carefully so as to have a feeling whether the coil engages with the opening of the catheter with consequent risk of damaging the coil. When the marking is pushed away from the cut and is again covered by the tube, the radiologist is certain that the most sensitive parts of the guidewire have been inserted fully into the catheter, whereupon the guidewire holder may be detached and removed.

In an alternative embodiment, the marking is only visible in the cut, when the flexible section of the guidewire has been inserted fully into the catheter. When the marking appears in the cut, the holder may be removed. In a particularly simple embodiment, the marking may consist of the proximal end of the guidewire.

BRIEF DESCRIPTION OF THE DRAWING

The invention will now be explained in further detail below with reference to the very schematic drawing of examples of preferred embodiments, in which

FIGS. 5 and 6 are enlarged sections of two different embodiments of the core in the distal end of the wire;

FIG. 7 is a view corresponding to that of FIG. 4 with an embolization coil threaded in.

DETAILED DESCRIPTION

Figures 1, 1A:
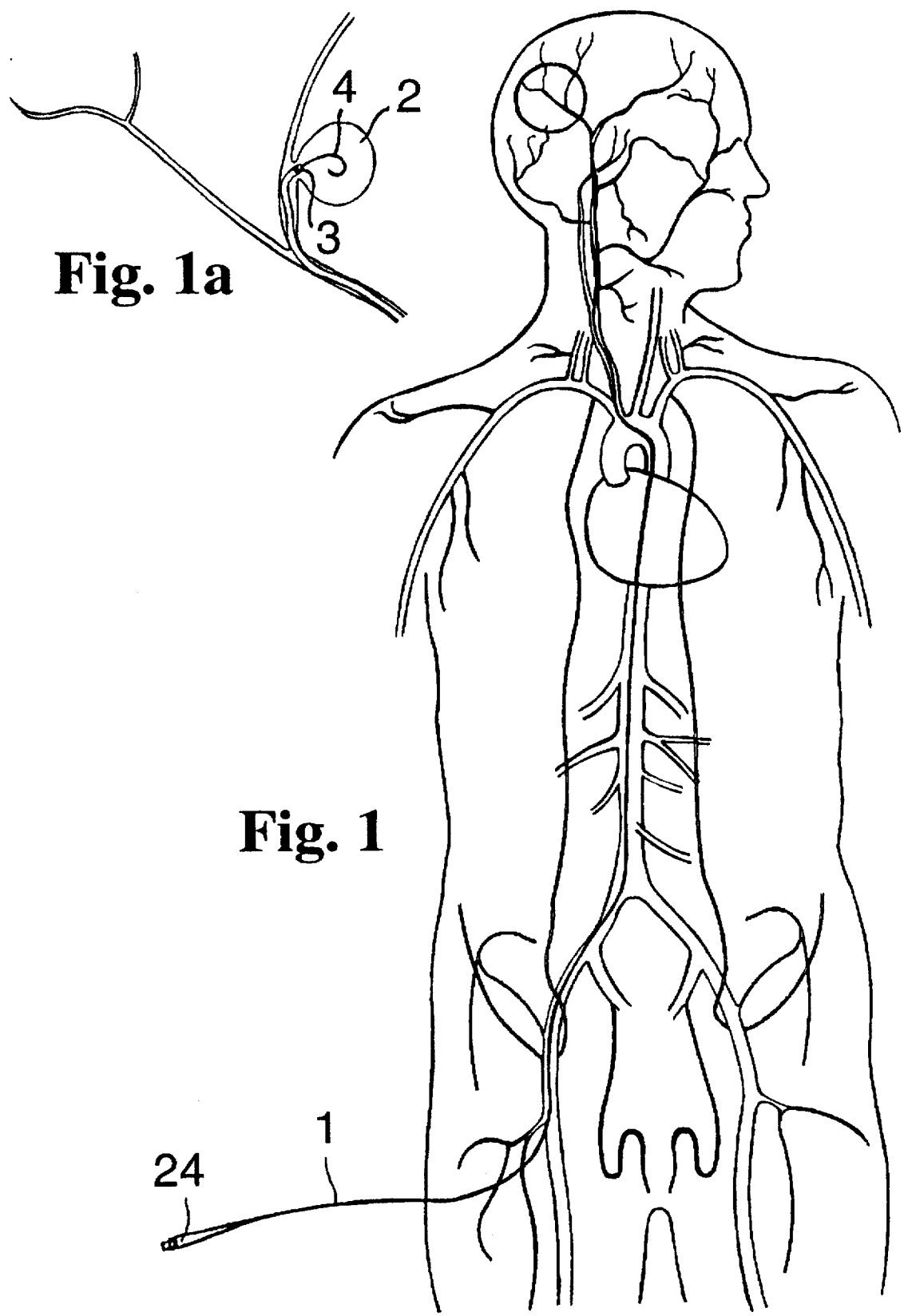
FIG. 1 shows a schematic view of a man with a transfemorally inserted superselective cerebral catheter.
FIG. 1a is a section marked by a circle in FIG. 1 of a cerebral vessel with the distal end of the catheter inserted in an aneurysm.

FIGS. 1 and 1a show a catheter 1 inserted into the femoral vein and further through the inferior and superior vena cavas and via one carotid vein up to an aneurysm 2 in a fourth order cerebral vessel branch, where the distal end 3 of the catheter has been directed in through the aneurysm opening out towards the vessel.

When the catheter is in place, the guidewire is removed, if one has been used at the insertion of the catheter. Then an embolization coil 4 is pushed through the catheter and out into the aneurysm as indicated in FIG. 1a, where the coil is on its way out into the aneurysm. This is done by passing a guidewire with an embolization coil threaded in through the catheter. The coil is usually premounted on the guidewire so that no time has to be used for the threading in of the coil, but it is also possible to thread in the coil immediately before insertion.

Guidewire in this context means any elongated flexible means of advancing a threaded-in embolization coil. Such a guide wire is also often called a pusher or a positioning wire.

Figure 2:
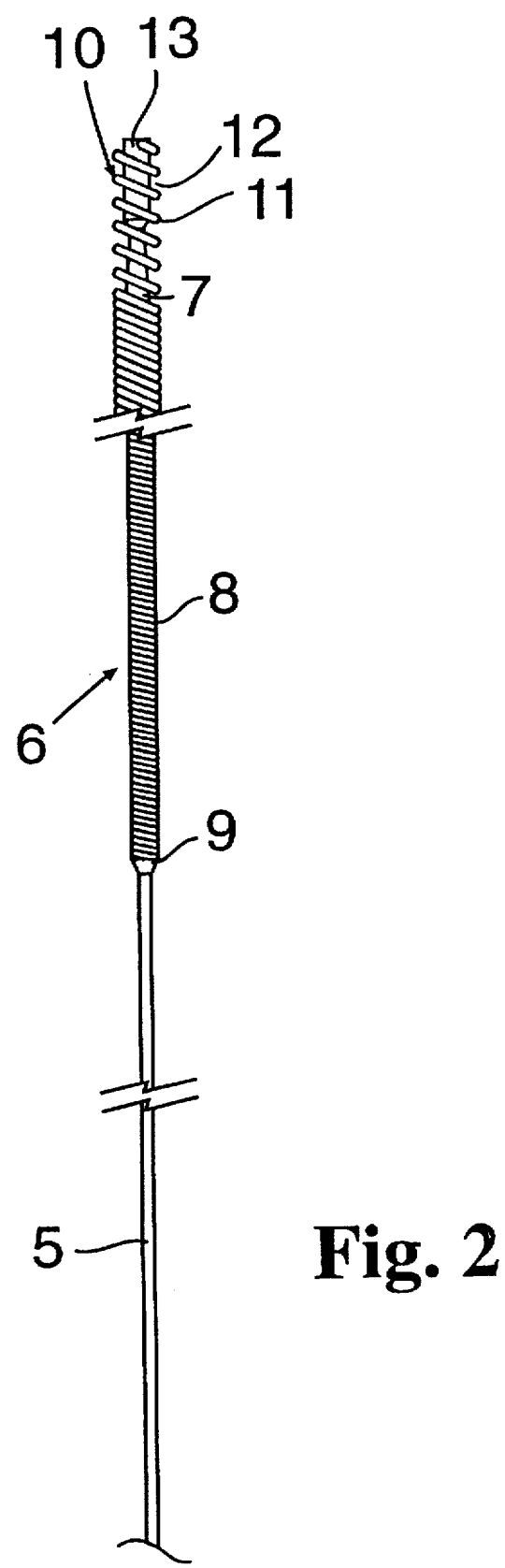
FIG. 2 is a section of a guidewire with an enlarged view of the distal end.

One embodiment of the guidewire is indicated in further detail in FIG. 2. The guidewire has an elongated body segment 5 of stainless steel or of another suitable material, such as nitinol, having a length of 60 to 250 cm and coated on its external side with a thin layer of friction-reducing material, such as polytetrafluoroethylene PTFE. The diameter of the body segment may be from 0.25 to 2 mm, depending on the relevant field of application. The body segment may typically be made of a single wire or rod, which may possibly be surrounded by a wirecoil or a wire braid.

The guidewire has a relatively more flexible distal section generally designated 6, comprising a central core 7 of stainless steel and a wirecoil 8 mounted on the outside of the core and fixed to the core at its proximal end 9 and at its distal end constituting a threading coil 10, as the turns 11 are here formed with a larger pitch so that they extend at a mutual spacing 12 into which the embolization coil may be threaded. The distal turns of the threading coil are fixed to an elongated member 13 at the distal end of the core, as will be explained in further detail below. The wire itself in the wirecoil and thus also in the threading coil may be of stainless steel and may have a wire diameter of from 0.02 to 0.12 mm, typically a diameter of about 0.075 mm. Over the major part of the length of the coil, the thread is wound at a pitch corresponding to the thickness of the wire so that the turns contact each other, but in the area of the threading coil, the wire may be wound at or pulled axially to a larger pitch with said spacing 12 between the turns. The outer diameter of the wound wire (the coil) may, for superselective use, be from 0.2 to 1 mm, typically from 0.35 mm to 0.45 mm.

Figure 4:
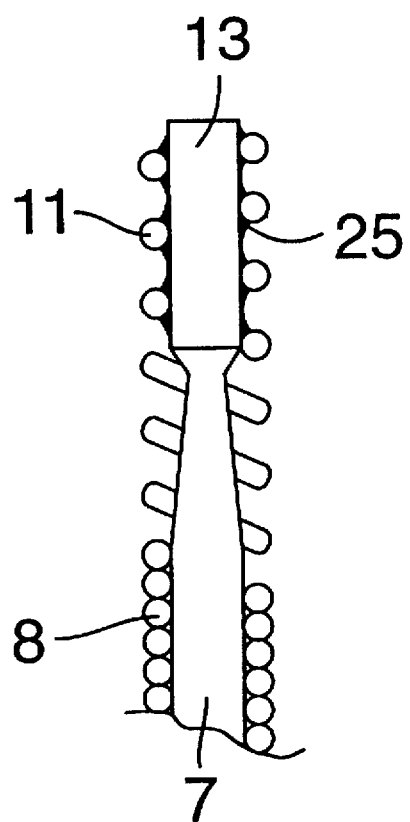
FIGS. 3 and 4 are enlarged sketches of the distal end of the guidewire before and after activation of a bonding layer.
Figure 3:
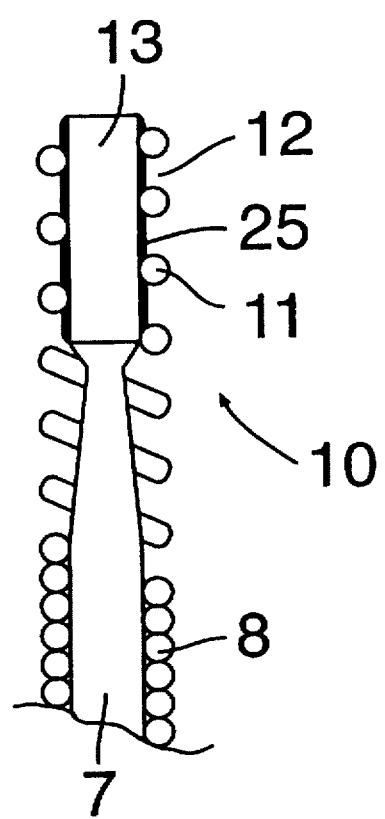

The fixation of the turns of the threading coil to the elongated member 13 is outlined in FIGS. 3 and 4, where the mutual dimensions of individual details are not realistic, but drawn so that the members are easily seen. On the external side of the member 13, a bonding layer 25 is applied, and the turns 11 are placed around the member in the desired helical shape as shown in FIG. 3. Then the bonding layer is activated so that the turns are fixed in the chosen geometry. If the material of the bonding layer can wet the wire material, the capillary forces between the internal side of the turns and the bonding layer cause the material to position itself some way up along the sides of turns so that an even transition occurs in the axial direction between the external side of the member and the turns. From FIG. 4 it is immediately clear that the resulting surface between the turns has a U-shaped course, which promotes the easy threading in and out of the embolization coil. Examples of applicable bonding layer materials in the form of plastic-based adhesives are a two-component adhesive "Activator No. 7649, adhesive No. 326" from Loctite, which cures on contact between the two components; an adhesive No. 3311 from Loctite; or an adhesive No. 136 from Dymax, where the two latter adhesives cure on irradiation with UV light.

The member 13 may typically have an external diameter of, for example 0.12 to 0.35 mm, typically 0.18 mm, before application of the bonding layer. In a preferred embodiment, the bonding material is tin solder. Before the turns are passed around the member 13, the latter is immersed in melted tin solder, whereby the layer 25 is applied in a thickness of from 0.001 to 0.003 mm, typically 0.002 mm, so that the surface becomes clean and smooth. Then the turns are placed around the member, and further tin solder is applied by renewed immersion in the melted tin solder or by application by means of a soldering iron. With a clean soldering iron, excess tin solder is drawn away from the turns during simultaneous activation of the bonding layer to result in the thread geometry as shown in FIG. 4.

The outer diameter of the member is usually selected so that the threaded-in embolization coil has an inner diameter which is at least 0.01 mm, preferably at least 0.03 mm larger than the "diameter" or the cross measure at the root of the finished thread. As the bonding layer adjusts itself at the activation to the geometry of the member 13 and the turns 11, the layer thickness may well deviate from the limits mentioned, which are merely preferred to ensure that on one hand there is sufficient bonding material to achieve an efficient fixation of the turns, and that on the other hand there is not any unnecessarily large excess of bonding material which may position itself between the turns in the finished thread.

Preferably, the member 13 and the threading coil 10 have dimensions so that from eight to twenty and, more preferably, from thirteen to fourteen turns are fixed to the external side of the member so that the embolization coil can be threaded about seven rotations into the thread before being pushed into the catheter. During the forward pushing of the coil to and testing in the aneurysm, this position of the coil in the thread gives the radiologist the liberty of rotating the coil six times in each direction without any risk.

When, as shown in the drawing, the threading coil 10 is constituted by the distal end of the wirecoil 8, it is easiest for manufacturing reasons to manufacture the threading coil with two or three excess turns, which in the completed guidewire will be located on the proximal side of the elongated member 13. If the threading coil is manufactured as an independent, helically shaped wire portion, for example because the flexible distal section of the guidewire is not surrounded by a wirecoil, the threading coil can still be made with a couple of excess turns, but preferably in that case the threading coil only has the required number of turns so that both the distal and the proximal ends of the threading coil are fixed to the external side of the member 13.

Two different embodiments of the central core 7 in the flexible distal section of the guidewire are shown in FIGS. 5 and 6, which have been drawn purely schematically, i.e. the lengths and thicknesses of the individual details do not exhibit their real proportions and mutual dimensions.

The core 7 is a distal extension of the body segment 5 and in addition to the member 13 the core comprises a proximal portion 14, 14' and an intermediate portion 15, 15' having a decreasing diameter towards the member 13 over at least part of its length. To produce a suitably large flexibility in the core, it normally has a proximal, conical segment 16 interconnecting the body segment and the proximal portion 14, 14', which may have the same diameter as the member 13. The total length of the segment 16 and the portion 14 is typically from 60 to 100 mm, and the length of the intermediate portion 15, 15' is typically from 300 to 600 mm, preferably 470 mm. When, as shown in FIG. 5, the intermediate portion 15 is cylindrical over, for example, two thirds of its proximal length, it may be connected with the portion 14 via a conical section 17 which reduces the diameter of the portion 15 by 10–25 percent in relation to the diameter of the portion 14. For example, the portion 15 may have a diameter of 0.145 mm, when the portion 14 has a diameter of 0.18 mm. Distally, the portion 15 is narrowed to a diameter immediately before the member 13 of about 40–60 percent of the outer diameter of the member.

In the preferred embodiment in FIG. 6, the intermediate portion is conical, evenly tapering towards the member 13, where the diameter is suddenly increased to the outer diameter of the member. The core 7 is produced from well-known materials and by means of the prior-art techniques usually applied for guidewires.

Figure 7:
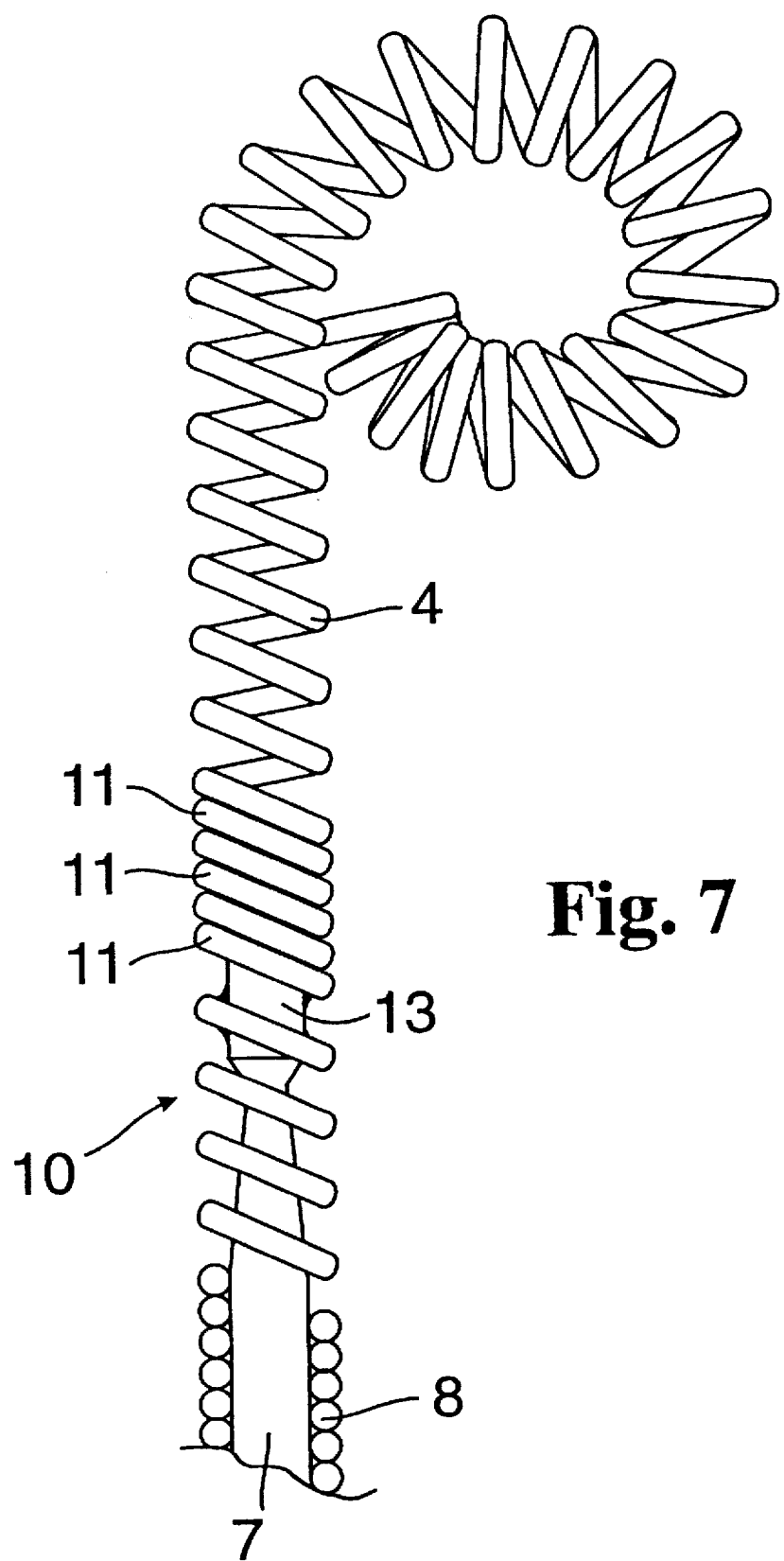

FIG. 7 shows an embolization coil 4 threaded into the thread of the guidewire and ready for insertion into the catheter. Embolization coils are well-known in the art and may be produced from platinum wire with coil lengths of between 5 and 300 mm and having different geometries in the unloaded state, such as straight, arcuate, figure-eight-shaped or more complicated shapes. The internal coil diameter may typically range from 0.14 to 0.45 mm, preferably about 0.20 mm. In a preferred embodiment, the coil is made from a wire having a wire diameter of 0.075 mm, wound up into an external coil diameter of about 0.38 mm (0.015 US inch). Regarding applicable geometries for embolization coils, please refer to the commercially available geometries for coils which are known, for example, from the company William Cook Europe under the trade names "Hilal Embolization Microcoils" and "MWCE Embolization Microcoils with Multiple Curls."

Figure 8:
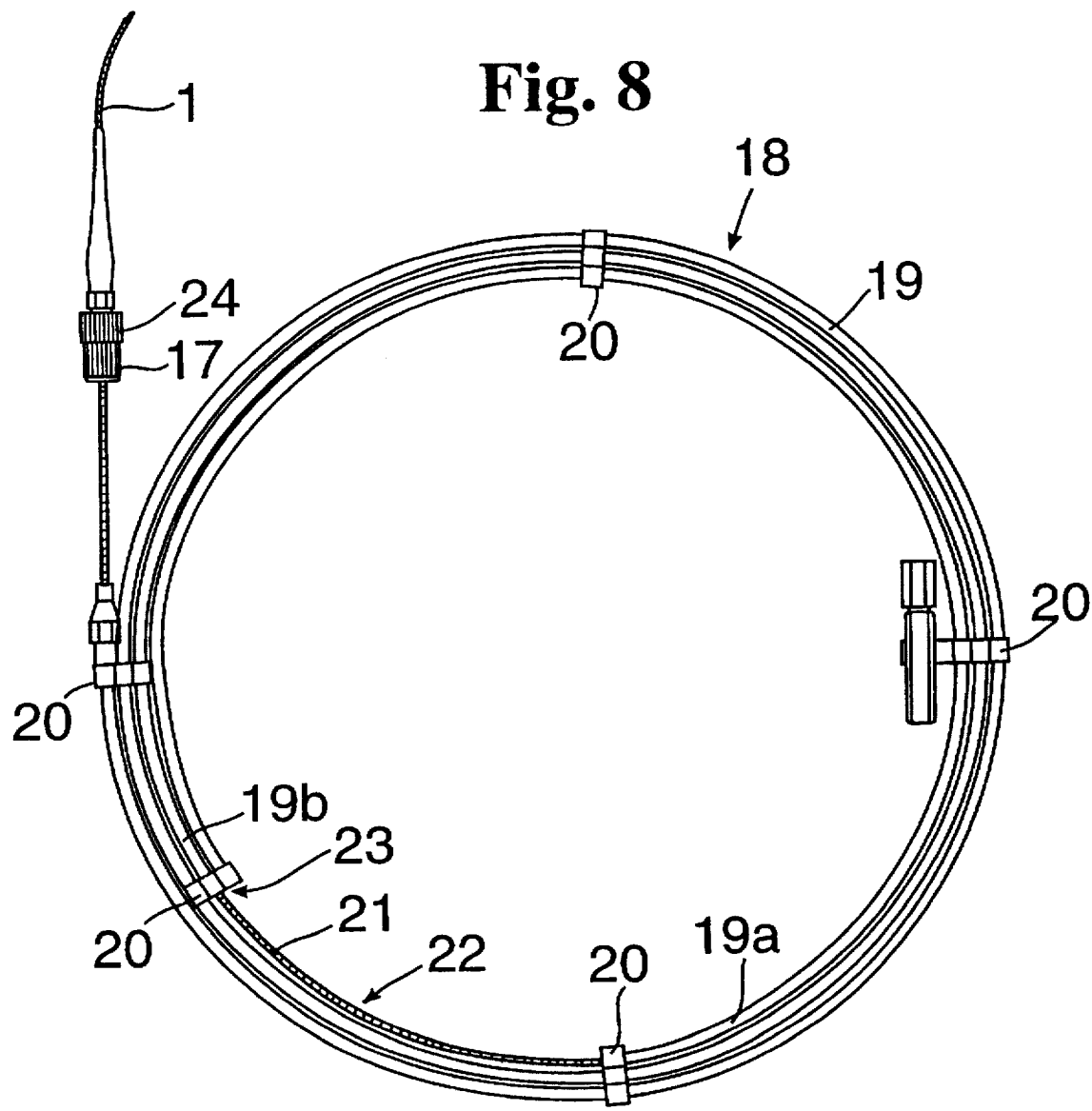
FIG. 8 is a plan view of a guidewire holder mounted on the proximal end of a catheter.

The proximal end of the catheter 1 has a coupling member 24 intended for coupling to a corresponding coupling means 17 on a guidewire holder 18 shown in FIG. 8, when the embolization coil is to be inserted into the catheter. The guidewire holder is constructed from a tube 19 of a suitably flexible plastic material, such as polyethylene. By means of several mounting fittings 20, the tube is arranged in a spiral shape. The mounting fittings may consist of two halves carrying cooperating snap locking means so that the halves can be arranged on respective sides of the rolled-up tube and be pressed together for fixation of the tube into the spiral shape. On its internal side, each half has several, for example three, semicylindrical depressions having a radius corresponding to the external radius of the tube. Alternatively, the tube can be fixed in the rolled-up shape by means of strip-shaped mounting fittings of a thermoplastic material which are simply pressed together around the tube under suitable thermal influence so that the strip portions melt together into a coherent mounting fitting. Normally, a mounting fitting is mounted at each end of the tube as well as a number, such as three, of mounting fittings distributed along the periphery of the rolled-up tube.

Between two of the mounting fittings 20, the tube is cut by removal of a piece of tube or by the tube being constituted by two tube lengths 19a, 19b. The tube 19 has a sufficient length for the whole guidewire to be placed inside the tube. The guidewire is provided with a marking 21, which is placed so that the marking is visible in the cut 22 when, at the pushing forwards of the guidewire through the tube, the embolization coil approaches the coupling member 17 at the transition to the catheter. The cut has a length so that at least the most flexible and thus sensitive part of the distal section 6 is passed into the catheter, when the marking 21 is pushed into the tube at the front end of the cut marked by the arrow 23. Alternatively, the marking may be so positioned in relation to the cut that the marking can be detected in the cut when the most flexible part of the section 6 has been inserted into the catheter.

When the catheter 1 is arranged in the patient, and the embolization coil can be inserted, the guidewire holder with the guidewire is mounted on the coupling means 24 of the catheter. Then the guidewire section positioned in the cut is gripped by the fingers to push it towards the front end of the cut so that the guidewire with the embolization coil is pushed towards the catheter 1. When the marking 21 indicates that the sensitive flexible part of the section 6 is inserted in the catheter, the radiologist can detach the holder from the coupling means 24 of the catheter and hold on to the guidewire in the cut while the holder is pulled so far back on the guidewire in a direction away from the catheter that the radiologist with his/her fingers can catch hold of the uncovered guidewire portion between the catheter and the coupling means 17 of the holder, and there maintain the position of the guidewire in relation to the catheter, while the holder is pulled completely free of the guidewire, whereupon the guidewire is passed up through the catheter in the conventional manner.

It is a substantial advantage that the embolization coil can be wrapped together with the guidewire in a sterile condition in the holder and be kept free of contact with the surroundings all the way until it has been inserted into the equally sterile catheter.

To prevent dislocation of the embolization coil after the detachment, it should meet the vessel wall to prevent it from freely turning round itself. This means, among other things, that the coil will be placed substantially locked against rotation in the vessel, if the coil is suitable, and detachment of the coil from the guidewire may therefore occur by the guidewire being rotated in the threading-out direction about its longitudinal axis, until the coil is threaded completely free of the threading coil 10.

What is claimed is:

1. An assembly for positioning an embolization coil (4) in a vascular system, comprising a guidewire having a relatively flexible distal section (6), which has a central core (7) and a threading coil (10) having distal turns (11), which are arranged with such mutual spacing (12) that the embolization coil can be threaded in and out of the threading coil; wherein the distal section (6) of the guidewire has an elongated, rotationally symmetrical member (13) having an outer diameter, which is a fraction smaller than an inner diameter of the embolization coil, and having a length, which is longer than at least three of the distal turns (11) of the threading coil; and wherein the distal turns of the threading coil are fixed to an external side of the member; wherein the central core (7) in the flexible distal section (6) of the guidewire comprises the member, a proximal portion (14; 14') and an intermediate portion (15; 15') with a decreasing diameter towards the member (13); and wherein the threading coil is a distal end of a wirecoil (8), a proximal end of which is fastened to said proximal portion.

2. An assembly according to claim 1 wherein the outer diameter of the member (13) is smaller than 0.25 mm, and its length is between 2 and 4 mm.

3. An assembly according to claim 1 wherein the outer diameter of the member (13) is in the interval from 0.25 to 0.36 mm.

4. An assembly according to claim 1 wherein the rotationally symmetrical member (13) has a decreasing diameter towards a distal end thereof.

5. An assembly according to claim 1, wherein at least five of the distal turns (11) of the threading coil are fixed to the external side of the member.

6. An assembly according to claim 5 wherein the rotationally symmetrical member (13) has a decreasing diameter towards a distal end thereof.

7. An assembly according to claim 1 wherein the proximal portion (14; 14') has substantially the same diameter as the member (13), wherein the intermediate portion (15; 15') tapers substantially evenly towards the member where the diameter is suddenly increased to the outer diameter of the member, and wherein the length of the member (13) is less than the length of the intermediate portion.

8. An assembly according to claim 7 wherein the rotationally symmetrical member (13) has a decreasing diameter towards a distal end thereof.

* * * * *